(12) United States Patent
Cho et al.

(10) Patent No.: US 8,999,456 B2
(45) Date of Patent: Apr. 7, 2015

(54) METHOD FOR MANUFACTURING OF DRUG-RELEASING STENT COATED WITH TITANIUM—OXIDE THIN FILM

(71) Applicant: Industry Foundation of Chonnam National University, Gwangju (KR)

(72) Inventors: Dong Lyun Cho, Gwangju (KR); Sun-Jung Song, Gwangju (KR); Myung Ho Jeong, Gwangju (KR); Kyoung Seok Kim, Gwangju (KR); Yu Jeong Park, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 364 days.

(21) Appl. No.: 13/673,140

(22) Filed: Nov. 9, 2012

(65) Prior Publication Data

US 2013/0129912 A1 May 23, 2013

Related U.S. Application Data

(62) Division of application No. 12/765,424, filed on Apr. 22, 2010.

(30) Foreign Application Priority Data

Jul. 9, 2009 (KR) .......................... 10-2009-0062571

(51) Int. Cl.
| | | |
|---|---|---|
| C23C 14/08 | (2006.01) | |
| A61F 2/82 | (2013.01) | |
| A61L 31/02 | (2006.01) | |
| A61L 31/08 | (2006.01) | |
| A61L 31/16 | (2006.01) | |
| C23C 16/40 | (2006.01) | |
| C23C 16/56 | (2006.01) | |
| A61F 2/86 | (2013.01) | |
| A61F 2/91 | (2013.01) | |

(52) U.S. Cl.
CPC ... *A61F 2/82* (2013.01); *A61F 2/86* (2013.01); *A61F 2/91* (2013.01); *A61F 2250/0067* (2013.01); *A61L 31/022* (2013.01); *A61L 31/088* (2013.01); *A61L 31/16* (2013.01); *A61L 2300/41* (2013.01); *A61L 2300/416* (2013.01); *A61L 2300/42* (2013.01); *C23C 16/405* (2013.01); *C23C 16/56* (2013.01)

(58) Field of Classification Search
USPC ......... 427/488, 525, 528, 529, 532, 535, 569; 623/1.15, 1.16, 1.46
See application file for complete search history.

(56) References Cited

U.S. PATENT DOCUMENTS

| | | | | |
|---|---|---|---|---|
| 5,023,078 | A | 6/1991 | Halluin | |
| 5,356,673 | A * | 10/1994 | Schmitt et al. | ................ 427/446 |
| 5,753,319 | A * | 5/1998 | Knapp et al. | .................. 427/529 |
| 2007/0264303 | A1 * | 11/2007 | Atanasoska et al. | .......... 424/423 |
| 2008/0004691 | A1 | 1/2008 | Weber et al. | |

FOREIGN PATENT DOCUMENTS

| | | |
|---|---|---|
| JP | 200247572 A | 2/2002 |
| JP | 2005168937 A | 6/2005 |
| KR | 1019990013643 | 3/1992 |
| KR | 1019990035927 | 5/1999 |
| KR | 1019990087472 | 12/1999 |
| KR | 1020000069536 | 11/2000 |
| KR | 1020020066707 | 8/2002 |
| KR | 1020020093610 | 12/2002 |
| KR | 1020030020476 | 3/2003 |
| KR | 1020037010759 | 2/2004 |
| KR | 1020040011463 A | 2/2004 |
| KR | 1020040055785 | 6/2004 |
| KR | 1020050004331 | 8/2005 |
| KR | 1020070003172 | 1/2007 |
| KR | 1020090074365 A | 7/2009 |
| WO | 2007133520 A2 | 11/2007 |

OTHER PUBLICATIONS

Kastrati et al. "Analysis of 14 Trails Comparing Sirolimus-Eluting Stents with Bare-Metal Stents", The New England Journal of Medecine, Mar. 8, 2007, pp. 1030-1039, vol. 356, No. 10.
Kim et al. "Production and reforming of titanium dioxide thin film through plasma process for production of drug-eluting stent excellent in biocompatibility", Department of Advanced Chemicals in Chonnam National University, Functional Nanomaterials Project by BK21, Research Institute for Catalysis in Chonnam National University, Apr. 22, 2009.

(Continued)

*Primary Examiner* — Ali Soroush
(74) *Attorney, Agent, or Firm* — The Webb Law Firm

(57) ABSTRACT

A method for manufacturing a drug-releasing stent is provided. The method includes providing a titanium precursor, a carrier gas and a reactant gas in a plasma vacuum chamber, and generating a plasma for 1 to 6 hours to form a titanium oxide thin film on the surface of a stent. The method further includes providing steam or oxygen and hydrogen in the plasma vacuum chamber and generating a low-temperature plasma for 10 minutes to 2 hours to modify the surface of the titanium oxide thin film. The method further includes reacting the titanium oxide thin film of the stent with a drug in an acidic solution and under an inert gas atmosphere at room temperature to 100° C. for 30 minutes to 4 hours to attach the drug.

6 Claims, 12 Drawing Sheets

(56) References Cited

OTHER PUBLICATIONS

McCafferty et al.; "Determination of the Concentration of Surface Hydroxyl Groups on Metal Oxide Films by a Quantitative XPS Method"; Surface and Interface Analysis; 1998; pp. 549-564; vol. 26.

Nan et al.; Blood Compatibility of Amorphous Titanium Oxide Films Synthesized by Ion Beam Enhanced Deposition; Biomaterials; 1998; pp. 771-776; vol. 19.

* cited by examiner

NT5

NT10

NT15

T5

T10

T15

| sample | NT5 | NT10 | NT15 | T5 | T10 | T15 |
|---|---|---|---|---|---|---|
| Rms | 3.571 | 5.142 | 7.119 | 7.760 | 9.403 | 13.862 |

T: titanium dioxide coated thin film, NT: nitrogen-doped titanium dioxide coated thin film, Numbers 5, 10 and 15 denote the discharge power used for the deposition of the titanium dioxide thin films.

FIG. 4A
| Name | PeakBE | FWHM eV | At.% |
|---|---|---|---|
| C1s | 285.02 | 2.54 | 33.89 |
| O1s | 530.45 | 2.52 | 48.24 |
| Ti2p | 458.9 | 2.25 | 17.87 |
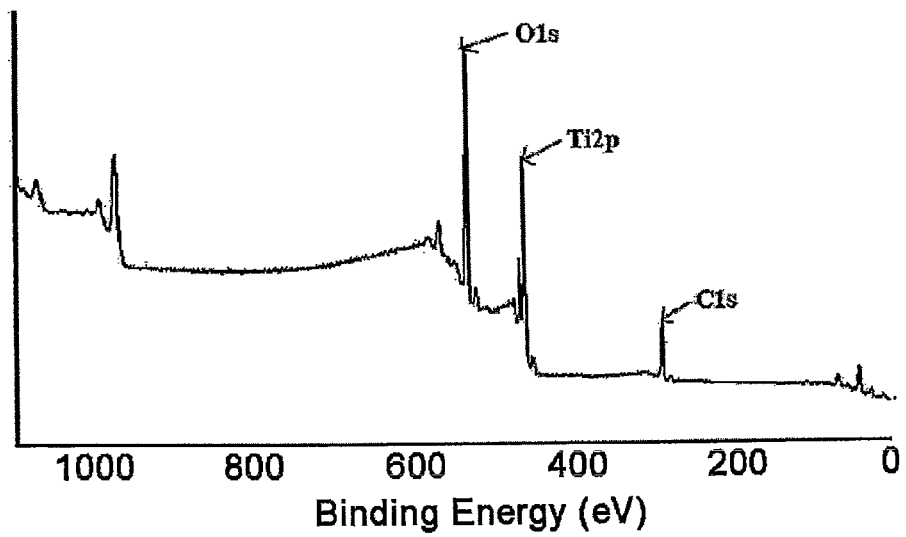
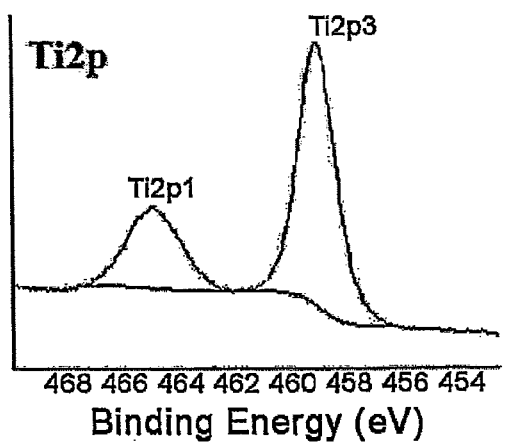
FIG. 4B
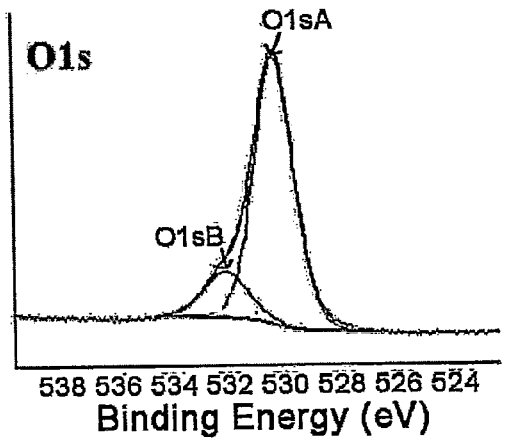
FIG. 4C FIG. 5A
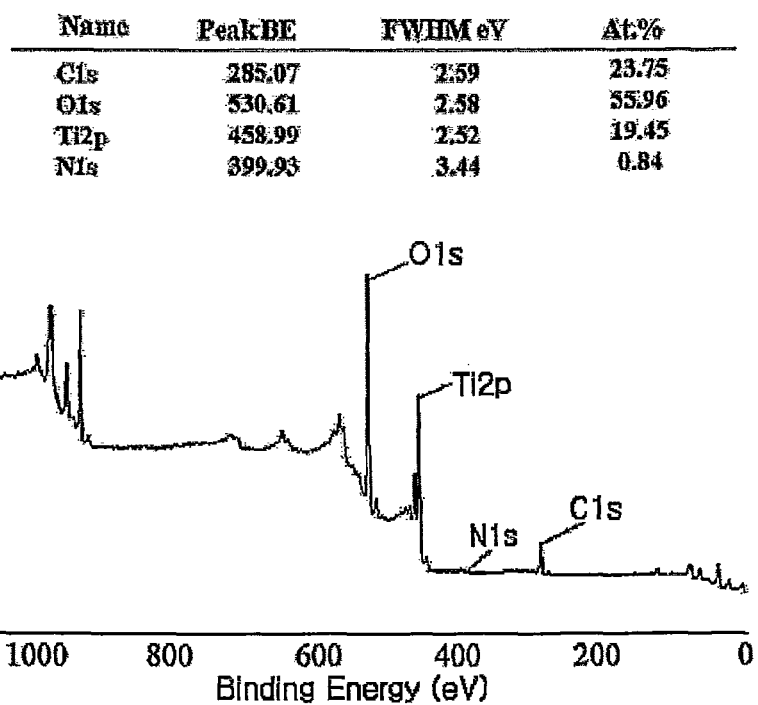
FIG. 5B    FIG. 5C    FIG. 5D
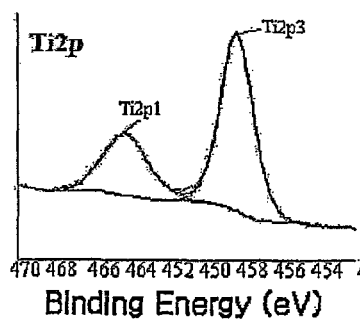 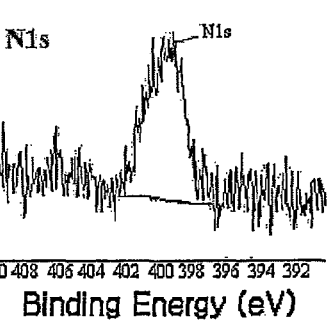 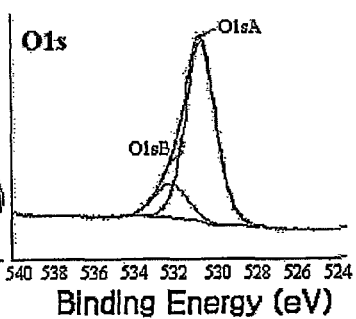

METHOD FOR MANUFACTURING OF DRUG-RELEASING STENT COATED WITH TITANIUM—OXIDE THIN FILM

CROSS-REFERENCES TO RELATED APPLICATIONS

This application is a division of co-pending U.S. patent application Ser. No. 12/765,424 filed Apr. 22, 2010, which claims priority of Korean Patent Application No. 10-2009-0062571, filed on Jul. 9, 2009, each of which are incorporated herein by reference in their entireties.

BACKGROUND OF THE INVENTION

1. Field of the Invention

The present invention relates to a drug-releasing stent which is inserted into a narrowed blood vessel to dilate the blood vessel and slowly releases a drug in the blood vessel, which is manufactured by coating the surface of the stent with titanium oxide, modifying the surface of the coated film, and chemically attaching the drug thereto.

2. Description of Related Art

A stent is a medical device inserted into a blood vessel narrowed due to various diseases to dilate the blood vessel and improve blood circulation. In general, the stent is inserted in heart blood vessels, aorta or brain blood vessels along with a balloon catheter, and the balloon is inflated to expand the coronary passage. As the balloon inflates, the stent expands outward and restores the blood vessel passage to its original state. Accordingly, the existing stent requires elasticity and ductility. That is to say, the stent requires ductility because it has to be inserted into complex and twisted passages. Further, upon insertion, elasticity is required to prevent deformation of the stent structure by the force applied from blood vessel tissues. For these reasons, corrosion-resistant stainless steel has been used to manufacture the stent. Although the introduction of metal-based stents avoids acute vessel closure and reduces restenosis after balloon angioplasty, restenosis in the stent resulting from neointimal hyperplasia during the restoration of the damaged blood vessel is becoming a problem. As an effort to prevent the restenosis, a drug is provided in the stent, so that the drug is supplied into the blood vessel after the insertion of the stent. This drug therapy inhibits cell proliferation and, thereby, supresses neointimal hyperplasia.

Meanwhile, recently, a technique of coating an aluminum thin film on the surface of a stainless steel stent, oxidizing the aluminum film to form a nanostructure having multiple pores, and injecting a drug into the pores in order to prevent restenosis in the blood vessel was disclosed in Korean Patent Publication No. 10-2004-0011463.

Since the stent inserted in the blood vessel is in direct contact with the blood vessel tissues, the surface of the stent should not be harmful to the human body. Further, a special technique is required to inject the drug into the stent.

Drug-releasing stents with organic compounds coated on the surface and drugs attached thereto are disclosed in Korean Patent Application No. 10-2005-0004331, Korean Patent Publication No. 10-2003-0020476 and others. However, the safety of the organic compound coated film has not been confirmed yet in terms of blood compatibility, cytotoxicity, or the like. In contrast, titanium oxide is biologically and biochemically safe and is widely used for cosmetics, food additives, or the like.

SUMMARY OF THE INVENTION

An object of the present invention is to provide a method for manufacturing a drug-releasing stent capable of expanding a narrowed blood vessel, releasing a drug in a sustained manner and remaining stable for a long time in the body without cytotoxicity.

To attain the object, the present invention provides a method for manufacturing a drug-releasing stent comprising: a titanium oxide layer coated with $TiO_2$ or $TiO_{2-x}N_x$ (wherein x is from 0.001 to 1) on a metal stent; and a drug coated layer with a drug attached on the titanium oxide layer.

More specifically, the present invention provides a method for manufacturing a drug-releasing stent, comprising: forming a titanium oxide [$TiO_2$ or $TiO_{2-x}N_x$ (wherein x is from 0.001 to 1)] thin film on the surface of a metal stent by plasma enhanced chemical vapor deposition (PECVD), modifying the thin film with a hydroxyl-substituted surface by a low-temperature plasma technique, and chemically attaching a drug thereto.

Thus manufactured drug-releasing stent remains stable for a long time in the blood vessel without cytotoxicity, provides superior blood compatibility, and releases a drug into the bloodstream in a sustained manner.

BRIEF DESCRIPTION OF THE DRAWINGS

FIG. 4A shows an electron spectroscopy for chemical analysis (ESCA) spectrum of a $TiO_2$ thin film deposited under the condition of 5 W, 4 h and 400° C.

FIG. 4B shows an electron spectroscopy for chemical analysis (ESCA) spectrum of a $TiO_2$ thin film deposited under the condition of 5 W, 4 h and 400° C.

FIG. 4C is a magnified is a magnified view of the electron spectroscopy analysis of FIG. 4. FIG. 5A shows an ESCA spectrum of a nitrogen-doped $TiO_2$ thin film deposited under the condition of 5 W, 4 h and 400° C.

FIG. 5B is a magnified is a magnified view of the electron spectroscopy analysis of FIG. 4A.

FIG. 5C is a magnified is a magnified view of the electron spectroscopy analysis of FIG. 4A.

FIG. 5D is a magnified is a magnified view of the electron spectroscopy analysis of FIG. 4A.

DESCRIPTION OF SPECIFIC EMBODIMENTS

Hereinafter, the present invention will be described in more detail.

Prior to manufacturing a drug-releasing stent according to the present invention, a metal stent suitable to expand a narrowed blood vessel needs to be selected. The metal stent of the present invention may be any known metal stent, without regard to type, length, weight, or the like. Preferred is one having such an excellent elasticity that it does not experience change in shape while remaining for a long time in the blood vessel in spite of the pressure inside the blood vessel or other environmental factors. Also preferred is one made of a non-corrosive and unharmful material. For example, the stents disclosed in Korean Patent Publication No. 10-2000-0069536, Korean Patent Publication No. 10-1999-0035927, Korean Patent Publication No. 10-1999-0087472, Korean Patent Publication No. 10-2002-0093610, Korean Patent Publication No. 10-2004-0055785, or the like may be used. Preferably, the metal stent is be made of a biocompatible metal material such as stainless steel, nitinol, tantalum, platinum, titanium, cobalt, chromium, cobalt-chromium alloy, cobalt-chromium-molybdenum alloy, etc. Further, other known biocompatible metal materials or composites with biocompatible metal materials may be used.

With regard to the method for manufacturing a drug-releasing stent of the present invention, the following description will be made with respect to a single metal stent unit, which refers to a single metal stent.

In the present invention, titanium oxide is deposited on the surface of the metal stent by means of plasma enhanced chemical vapor deposition (PECVD) of a titanium precursor.

Figure 1:
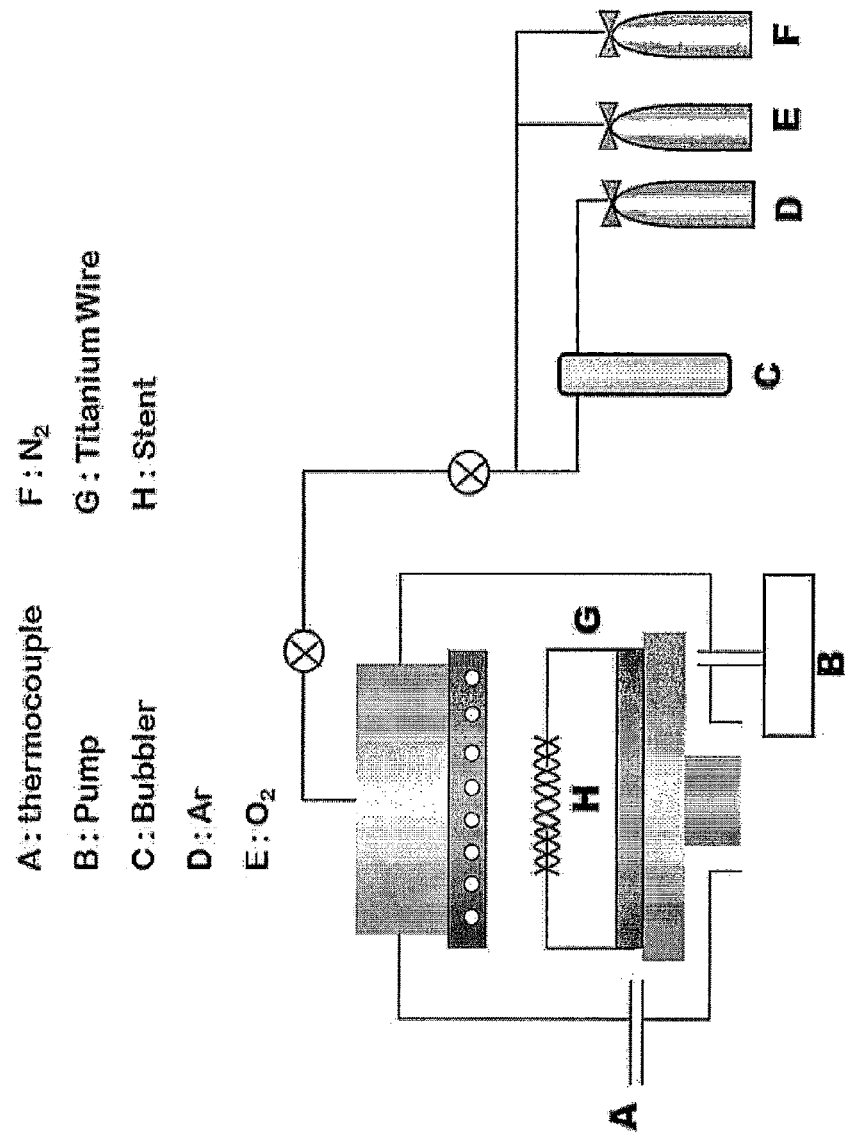
FIG. 1 schematically shows a plasma enhanced chemical vapor deposition (PECVD) apparatus for forming a titanium dioxide or nitrogen-doped titanium dioxide thin film.

In the present invention, PECVD may be performed using a commonly known PECVD apparatus. For example, the PECVD apparatuses disclosed in Korean Patent Application No. 10-2005-0058926, Korean Patent Application No. 10-2001-0007030, Korean Patent Application No. 10-1990-0013643, or the like may be employed. Preferably, as illustrated in FIG. 1, a PECVD apparatus equipped with a titanium wire G for fixing a stent in a plasma chamber, a decompression pump B connected to the plasma chamber, and a bubbler C containing a titanium precursor and connected to gas tanks D, E, F so as to supply a vapor of the precursor into the plasma chamber along with other gases may be used.

The present invention provides a method for manufacturing a drug-releasing stent, comprising:

(a) providing a titanium precursor, a carrier gas and a reactant gas in a plasma vacuum chamber and generating a plasma for 1 to 6 hours to form a titanium oxide thin film on the surface of a stent;

(b) providing steam or providing oxygen and hydrogen in the plasma vacuum chamber and generating a low-temperature plasma for 10 minutes to 2 hours to modify the surface of the titanium oxide thin film; and (c) reacting the titanium oxide thin film of the stent with a drug in an acidic solution and under an inert gas atmosphere at room temperature to 100° C. for 30 minutes to 4 hours to attach the drug.

In the present invention, for the titanium precursor to deposit titanium oxide on the metal stent, one or more selected from a group consisting of titanium butoxide, tetraethylmethylamino titanium, titanium ethoxide, titanium isopropoxide and tetramethylheptadiene titanium may be used. Besides, any known titanium precursor that provides superior deposition of titanium oxide on the metal stent by PECVD may be used.

In the present invention, prior to the deposition of titanium oxide on the metal stent, the metal stent is fixed in the plasma vacuum chamber and the surface of the metal stent is pretreated by cleaning. The pretreatment is performed to enhance deposition of the titanium oxide thin film on the stent, and is carried out by flowing a gas mixture of argon and oxygen while maintaining the temperature in the plasma vacuum chamber at 200 to 600° C.

In the present invention, the titanium oxide deposited on the metal stent has two meanings. One is titanium dioxide ($TiO_2$) formed as oxygen is bound to titanium, and the other is nitrogen-doped titanium dioxide ($TiO_{2-x}N_x$; x is from 0.001 to 1) formed as nitrogen is doped into titanium dioxide. The titanium dioxide may have any crystal structure and may be in any form including rutile, anatase and brookite. The thin film of the two types of titanium oxide is formed on the surface of the metal stent by providing the carrier gas and the titanium precursor and generating a plasma while flowing the reactant gas. Either of the two types of titanium oxide is formed depending on the kind and flow rate of the reactant gas. For the carrier gas, one or more gas selected from a group consisting of argon and helium may be flown along with the titanium precursor, so that the carrier gas and the titanium precursor are introduced into the plasma chamber. Then, if a plasma is generated by flowing oxygen only, titanium dioxide is deposited on the surface of the metal stent. And, if nitrogen is flown along with oxygen, nitrogen-doped titanium dioxide is deposited on the surface of the metal stent. Accordingly, it is preferred to select a nitrogen-free carrier gas to deposit titanium dioxide ($TiO_2$) on the metal stent. As described above, titanium dioxide has proven biological and biochemical safety. And, nitrogen-doped titanium dioxide, which is obtained by doping titanium dioxide with nitrogen, is reported to have improved antithrombotic effect by Kasrtari A et al. (Kastrati A, Mehilli J, Pache J, Kaiser C, Valgimigli M, Kelbaek H, Menichelli M, Sabate M, Suttorp M J, Baumgart D, Seyfarth M, Pfisterer M E, Schomig A. *N. Engl. J. Med.*, 356, 1030, 2007).

In the present invention, it is preferred that a bubbler is used to introduce the titanium precursor into the plasma chamber in gas phase. The bubbler may be preheated at a temperature range adequate to vaporize the titanium precursor, i.e. from room temperature to the boiling temperature of the titanium precursor, and then the carrier gas may be passed through the bubbler to be transferred to the plasma chamber. At this time, oxygen or oxygen and nitrogen may be transferred together to form titanium dioxide or nitrogen-doped titanium dioxide.

After the introduction of the titanium precursor, the carrier gas and the reactant gas into the plasma chamber, a plasma is generated in the plasma chamber to perform chemical deposition on the surface of the metal stent. The carrier gas may be flown at a rate of 50 to 500 sccm, preferably at 100 to 200 sccm, and the reactant gas may be flown at a rate of about 10% that of the carrier gas, preferably at 10 to 100 sccm. In case the carrier gas is a mixture of oxygen and nitrogen, the flow rate of oxygen:nitrogen may be 1 to 9:9 to 1.

In the present invention, after the titanium precursor, the carrier gas and the reactant gas are provided in the plasma vacuum chamber, the plasma is generated to deposit titanium oxide on the surface of the metal stent. The discharge power of the plasma may be 1 to 300 W and the reaction may be performed for 1 to 6 hours, more preferably at 5 to 200 W for 3 to 5 hours.

After the above procedure, the titanium oxide thin film formed on the metal stent may have a thickness of 10 to 500 nm, preferably 20 to 200 nm.

Figure 2A:
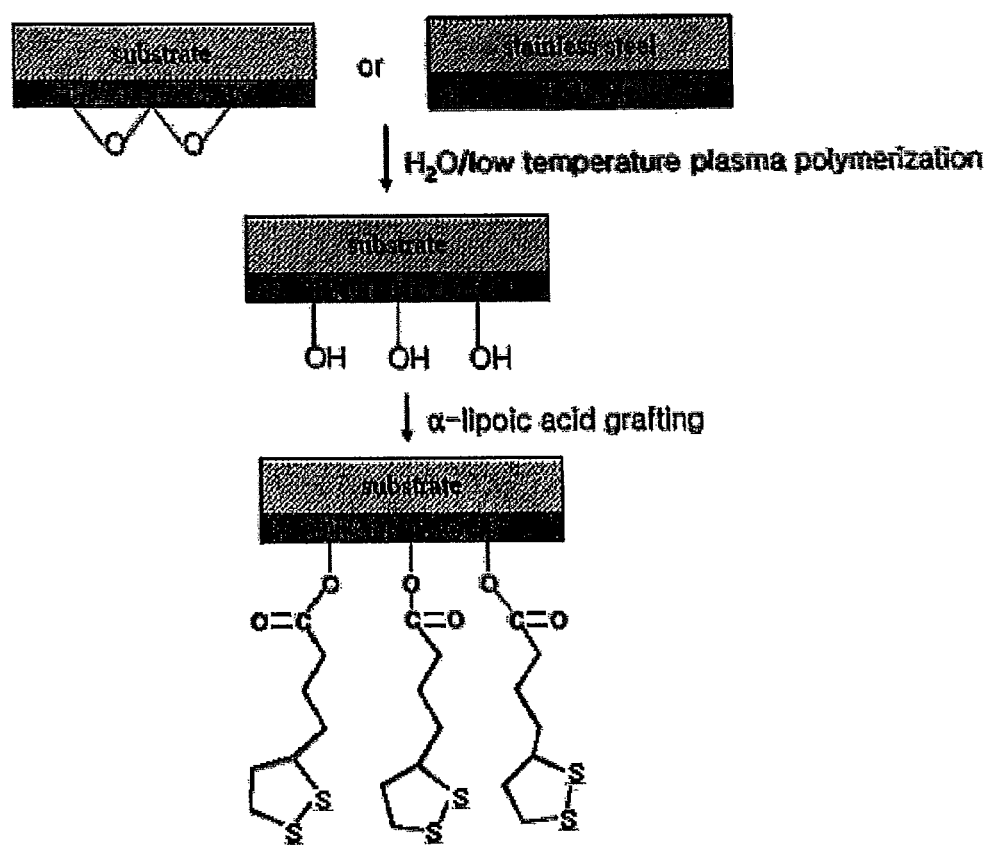
FIG. 2A schematically shows a procedure of manufacturing an α-lipoic acid coated stent, according to an embodiment of the invention.

In the present invention, the surface of the titanium oxide coated film is modified by introducing hydroxyl (—OH) groups in order to attach the drug on the titanium oxide coated film of the metal stent. The surface modification is performed inside the plasma vacuum chamber wherein the titanium oxide film has been formed. It may be performed by providing steam ($H_2O$) or a gas mixture of hydrogen and oxygen instead of steam into the plasma vacuum chamber from a supply tube connected to the plasma vacuum chamber under a vacuum of $1 \times 10^{-3}$ to 1 torr, preferably $1 \times 10^{-2}$ to $1 \times 10^{-1}$ torr. Preferably, the steam or the gas mixture of hydrogen and oxygen is provided at a rate of 1 to 50 sccm based on the unit stent. After the steam or the gas mixture of hydrogen and oxygen is introduced into the plasma chamber, a plasma is generated to modify the surface oxygen of the titanium dioxide or nitrogen-doped titanium dioxide film with hydroxyl groups, as illustrated in FIG. 2A. The plasma discharge power may be 1 to 300 W and the reaction time may be 10 minutes to 2 hours.

The titanium oxide thin film coated on the surface of the metal stent is modified with hydroxyl groups because the drugs used in the present invention have carboxyl, aldehyde or alcohol functional groups and thus may be easily bound on the surface of the titanium oxide through dehydration with the hydroxyl groups of the modified titanium oxide film under an acidic condition. Since the drugs having various functional groups are physically attached on the surface of the stent in several layers, upon insertion into the blood vessel, the drug-releasing stent may release the drug physically attached thereto in a sustained manner, while maintaining the inherent structures of the titanium oxide and the drug.

Figure 2B:
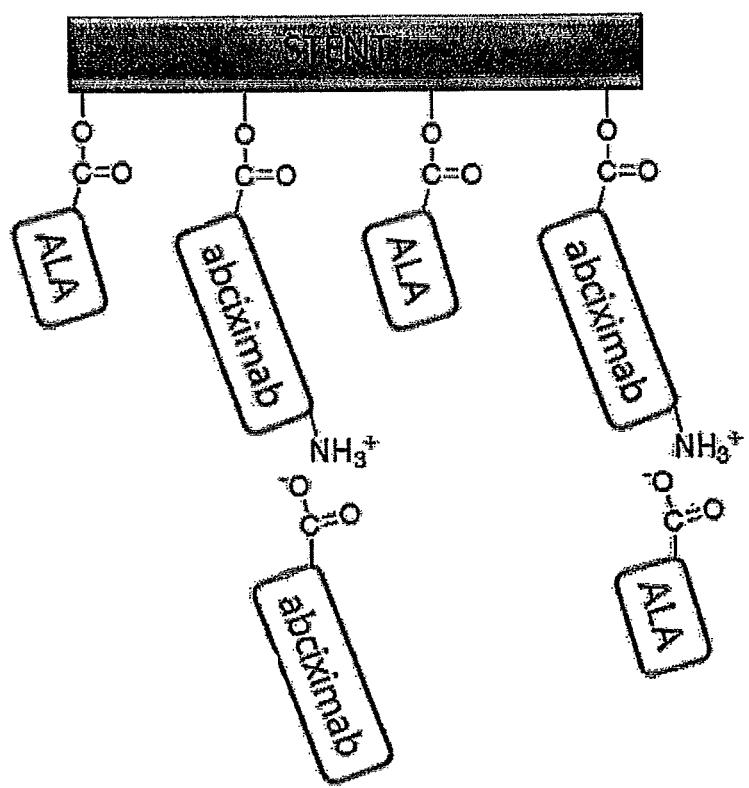
FIG. 2B schematically shows an α-lipoic acid coated stent, according to an embodiment of the invention.
Figure 3A:
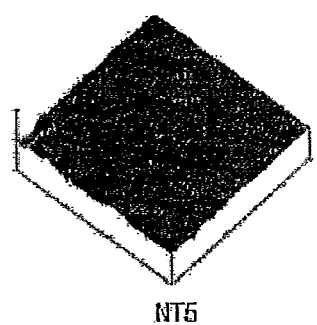
FIG. 3A shows an atomic force microscopy (AFM) image of the surface coated with nitrogen-doped titanium dioxide, according to an embodiment of the invention.
Figure 3B:
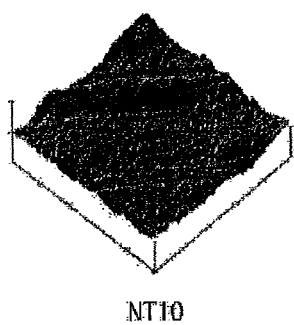
FIG. 3B shows an atomic force microscopy (AFM) image of the surface coated with nitrogen-doped titanium dioxide, according to an embodiment of the invention.
Figure 3C:
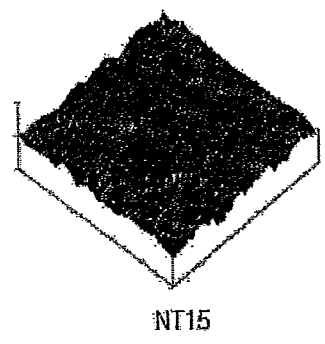
FIG. 3C shows an atomic force microscopy (AFM) image of the surface coated with nitrogen-doped titanium dioxide, according to an embodiment of the invention.
Figure 3D:
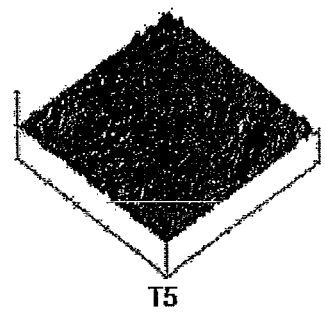
FIG. 3D shows an atomic force microscopy (AFM) image of the surface coated with titanium dioxide according to an embodiment of the invention.
Figure 3E:
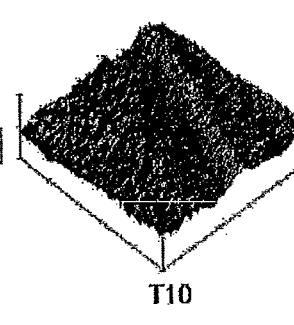
FIG. 3E shows an atomic force microscopy (AFM) image of the surface coated with titanium dioxide, according to an embodiment of the invention.
Figure 3F:
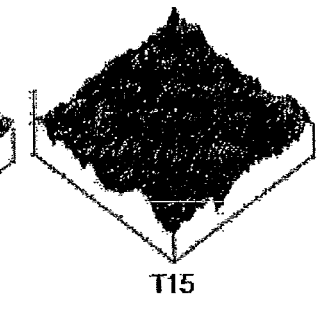
FIG. 3F shows an atomic force microscopy (AFM) image of the surface coated with titanium dioxide, according to an embodiment of the invention.

In the present invention, the drug attached on the titanium oxide thin film coated on the metal stent may be a drug capable of inhibiting neointimal hyperplasia or blood clot formation. For example, it may be one or more drug(s) selected from a group consisting of an anticancer drug, an anti-inflammatory drug, a smooth muscle cell growth inhibitor and an antithrombotic drug. Only one drug may be physically or chemically bound on the surface of the titanium oxide layer, so that it may be released in the body. Alternatively, two or more different drugs may be independently bound on the surface of the titanium oxide layer to give a multidrug-releasing stent that releases two or more drugs. In case the drug is a mixture of two or more drugs, each of the drugs may be individually dispersed and bound directly on the surface of the titanium oxide coated film or two or more of the drugs may be physically or chemically bound to each other by electrostatic attractions, hydrogen bonds, etc. between the drugs and then bound on the titanium oxide coated film (see FIG. 2B). For example, if lipoic acid and ReoPro are bound on the titanium oxide thin film together, lipoic acid may provide anti-inflammatory effect and ReoPro may improve anti-thrombotic effect.

In the present invention, the drug that may be bound on the titanium oxide thin film of the metal stent includes all the drugs that may be bound to the hydroxyl groups introduced on the surface of titanium oxide through the surface modification. Especially, a drug having one or more functional group(s) selected from carboxyl, aldehyde and alcohol functional groups is easily bound on the titanium oxide thin film of the metal stent. Therefore, in the present invention, the drug may be one or more selected from an anticancer drug, an anti-inflammatory drug, a smooth muscle cell growth inhibitor and an antithrombotic drug having one or more functional group(s) selected from carboxyl, aldehyde and hydroxyl groups.

Examples of the drugs include molsidomine, linsidomine, nitroglycerin, hydralazine, verapamil, diltiazem, nifedipine, nimodipine, captopril, enalapril, lisinopril, quinapril, losartan, candesartan, irbesartan, valsartan, dexamethasone, betamethasone, prednisone, corticosteroid, 17β-estradiol, cyclosporine, mycophenolic acid, tranilast, meloxicam, celebrex, indometacin, diclofenac, ibuprofen, naproxen, reserpine, hirudin, hirulog, agatroban, sirolimus (rapamycin), rapamycin derivatives, paclitaxel, 7-hexanoyltaxol, cisplatin, vinblastine, mitoxantrone, combretastatin A4, topotecan, methotrexate, flavopiridol, actinomycin, ReoPro (abciximab), α-lipoic acid, heparin, warfarin, aspirin, abiprofen, prostacyclin, or the like. Preferably, one or more selected from heparin, ReoPro (abciximab), α-lipoic acid, sirolimus (rapamycin), actinomycin, molsidomine, linsidomine and paclitaxel may be used.

In the method for manufacturing a drug-releasing stent according to the present invention, the procedure (c) is performed by adding the titanium oxide coated film metal stent with the hydroxyl groups introduced to a separate reactor, mixing it with the drug and stirring in an acidic solution under an inert gas atmosphere, after further adding distilled water or an organic solvent if necessary.

Preferably, the distilled water may be ultrapure distilled water such as triple distilled water. And, preferably, the organic solvent may also be an ultrapure organic solvent with a purity 99.999% or better which hardly contains impurities. The acidic solution serves the role of a catalyst in the reaction of the titanium oxide layer coated metal stent with the drug. Preferably, the acidic solution is selected from sulfuric acid, nitric acid and hydrochloric acid. Most preferably, sulfuric acid is used. Preferably, the acidic solution is used in an amount of 10 to 100 μL based on the unit metal stent. For the inert gas, nitrogen, helium, argon, or the like may be used. Preferably, all inert gas used in the manufacturing of a drug-releasing stent according to the present invention is ultrapure gas with a purity 99.999% or better.

The procedure (c) may be performed by stirring at room temperature to 100° C. for 30 minutes to 4 hours, preferably at 50 to 70° C. for 1 to 2 hours.

After the reaction is completed, the stent may be recovered and cleaned according to a cleaning method known in the art. Preferably, it may be washed with an ultrapure alcohol solvent, washed several times with triple distilled water, and then dried to prepare a drug-releasing stent for insertion into the blood vessel.

The chemical composition of the surface of thus manufactured drug-releasing stent may be analyzed by attenuated total reflectance (ATR) Fourier transform infrared spectroscopy (FT-IR) (FT/IR 430, Miracle, Jasco) and electron spectroscopy for chemical analysis (ESCA) (VG Multilab 2000, ThermoVG Scientific). The surface state may be analyzed using a scanning electron microscope (SEM, S-4700, Hitachi). The roughness and coating state of the thin film may be examined by atomic force microscopys (AFM). Further, the introduction of functional groups on the surface of the titanium dioxide thin film may be confirmed by measuring contact angle of the thin film surface with water before and after the surface modification using a contact angle analyzer (G-1, Erma). The binding of the titanium dioxide thin film with the stent and the integrity thereof may be examined by scanning electron microscopy (SEM) after treating the titanium dioxide coated stent for 30 minutes using an ultrasonic cleaner. Drug release test may be performed as follows. The stent is immersed in 1×PBS buffer and stirred in an incubator at 30 to 50° C., preferably 35 to 40° C., while changing the PBS buffer every day. Then, the amount of the drug released into the PBS buffer is measured based on UV absorption.

In accordance with the present invention, a thin film layer of titanium dioxide ($TiO_2$) or nitrogen-doped titanium dioxide ($TiO_{2-x}N_x$; x is from 0.001 to 1), which are known to have superior antithrombotic effect and biocompatibility, is coated on a metal stent to attach a drug to the metal stent. Since the PECVD technique employed for the thin film coating is known to give an impurity-free, uniform and stable thin film, it is considered suitable to deposit a stable thin film on the surface of the stent. Further, since titanium dioxide is biologically and biochemically safe, being widely used for cosmetics, food additives, or the like, and inexpensive, it is suitable as a thin film material of the drug-releasing stent. Especially, it is reported that nitrogen doping of the titanium dioxide thin film further enhances antithrombotic effect. When coating the titanium dioxide layer, a more uniform thin film is attained at a lower discharge power. Given the same discharge power, a nitrogen-doped titanium dioxide thin film prepared using a mixture of oxygen and nitrogen features a more uniform surface than an undoped titanium dioxide thin film. The drug-releasing stent manufactured in accordance with the present invention exhibits superior adhesion between the drug bound thin film layer and the stent and features uniform surface without tearing or digging. Accordingly, it is considered that the coated thin film may remain firm without being detached from the stent during sterilization for insertion into the blood vessel or by the bloodstream, and have superior blood compatibility. Further, if two or more drugs, such as heparin and α-lipoic acid or ReoPro and α-lipoic acid, are attached on the modified surface of the stent, the shortcoming of a single-drug stent may be resolved and α-lipoic acid may be released over a long period of time in a sustained manner.

EXAMPLES

The examples and experiments will now be described. The following examples and experiments are for illustrative purposes only and not intended to limit the scope of this disclosure.

Example 1

Preparation of Titanium Dioxide and Nitrogen-Doped Titanium Oxide ($TiO_{2-x}N_x$) Thin Films A stent was fixed in a vacuum chamber connected to a radio frequency (RF) plasma generator and a vacuum pump using a titanium wire, as illustrated in FIG. 1. The temperature inside the plasma chamber was maintained at 400° C. In order to improve adhesion between the stent and a thin film, the surface of the stent was cleaned by a plasma pretreatment process by flowing argon and oxygen, prior to the coating of the thin film. After adding titanium isopropoxide in a bubbler, the titanium isopropoxide was mixed with oxygen, a reactant gas, and introduced into the reaction chamber using argon as a carrier gas, while maintaining the temperature of the bubbler at 50° C. Then, a plasma was generated for 4 hours to coat a titanium dioxide thin film on the surface of the stent. The carrier gas argon was supplied at a rate of 100 sccm, and the reactant gas oxygen was supplied at a rate of 20 sccm. Various thin films were formed while varying discharge power from 5 to 200 W. Nitrogen-doped titanium dioxide thin films were prepared in a similar manner, while supplying argon at a rate of 100 sccm, oxygen at 10 sccm, and nitrogen at 1 sccm.

Example 2

Modification of Titanium Oxide Thin Film With Hydroxyl Groups

In order to chemically attach a drug on the surface of the coated titanium dioxide, the titanium oxide should have functional groups that can chemically bind to the functional groups of the drug molecules. Accordingly, the surface of titanium dioxide was modified using a low-temperature plasma and distilled water ($H_2O$) in order to introduce hydroxyl (—OH) groups thereon. The titanium dioxide coated stent was fixed in a tubular low-temperature plasma reactor made of Pyrex. After filling triple distilled water in a bubbler, steam was supplied into the plasma reactor at a rate of 10 sccm. The titanium dioxide thin film was modified for 10 minutes via a low-temperature plasma process while varying discharge power from 10 to 100 W. The result of surface modification was confirmed by measuring a contact angle.

Example 3

Manufacture of α-lipoic Acid Attached Stent

A two-neck round flask connected to a reflux condenser was purged with nitrogen, and the surface-modified unit stent, α-lipoic acid (0.5 g), distilled water (5 mL) and strong sulfuric acid (20 μL) were added thereto. The mixture was stirred for 1 hour under a nitrogen atmosphere while maintaining the temperature at 55° C. Upon completion of the reaction, the stent was recovered, washed 3 times with ethanol, washed 3 times with flowing triple distilled water, blown with air, and dried in a desiccator.

Example 4

Manufacture of α-lipoic Acid-ReoPro Attached Stent

The surface-modified unit stent, α-lipoic acid (0.5 mL, 25 mg/mL, thioctic acid 600T, Viatris GmbH & Co. KG), ReoPro (2 mL, 5 mg/mL, Eli Lilly and Company, Indianapolis, Ind.), distilled water (10 mL) and strong sulfuric acid (40 μL) were added to a reactor configured in the same manner as Example 3. The mixture was stirred for 1 hour under a nitrogen atmosphere while maintaining the temperature at 55° C. Upon completion of the reaction, the stent was washed and dried in the same manner as Example 3.

Evaluation

In order to measure the quantity of α-lipoic acid and ReoPro attached to the stent, standard solutions with four concentrations were prepared for each drug. Absorbance was measured using a UV spectrometer (Shimadzu 1601, Japan) at 330 nm for α-lipoic acid and at 278 nm for ReoPro. Thus, calibration curves were drawn for α-lipoic acid and ReoPro. Then, in order to measure the quantity of the drugs attached to the stent, each 500 μL of the reaction solution was taken before and after the reaction, which were diluted by mixing with triple distilled water (2.5 mL) and subjected to absorbance measurement at 278 nm and 330 nm, respectively. The measurement result was compared with the calibration curves to determine the quantity of α-lipoic acid and ReoPro attached to the stent.

(a) Analysis of Physical and Chemical Structure of Thin Film

The chemical composition of the surface of the modified and drug attached stent was analyzed by attenuated total reflectance (ATR) Fourier transform infrared spectroscopy (FT-IR) (FT/IR 430, Miracle, Jasco) and electron spectroscopy for chemical analysis (ESCA) (VG Multilab 2000, ThermoVG Scientific). The surface state was analyzed by scanning electron microscopy (SEM, S-4700, Hitachi). The roughness and coating state of the thin film was examined by atomic force microscopy (AFM). Further, the introduction of functional groups on the surface of the titanium dioxide thin film was confirmed by measuring contact angle of the thin film surface with water before and after the surface modification using a contact angle analyzer (G-1, Erma). The binding of the titanium dioxide thin film with the stent and the integrity thereof were examined by SEM after treating the titanium dioxide coated stent for 30 minutes using an ultrasonic cleaner. Drug release test was performed as follows. The stent was immersed in 1× PBS buffer and stirred in an incubator at 37° C., while changing the PBS buffer every day. Then, the amount of the drug released into the PBS buffer was measured based on UV absorption.

(b) Analysis of Surface Characteristics of Titanium Dioxide and Nitrogen-Doped Titanium Dioxide Coated Stents The coating of the titanium dioxide thin film may be performed at various discharge powers from 5 to 200 W. In order to investigate the effect of discharge power on surface roughness, experiments were performed at different discharge powers of 5, 10 and 15 W. The results are shown in FIGS. 3A-3F. In the table inserted in FIGS. 3A-3F, the root mean square (RMS) thickness values of the thin films prepared at 400° C. for 4 hours at different discharge powers of 5, 10 and 15 W. Atomic force microscopys (AFMs) are also shown in FIGS. 3A-3F. As seen from FIGS. 3A-3F, the nitrogen-doped titanium dioxide thin films showed better surface uniformity than the titanium dioxide thin films, and a more uniform thin film could be attained at lower discharge power. The blood compatibility is affected by the roughness of thin film. It is known that less surface roughness results in better blood compatibility.

The film prepared at 5 W had the lowest surface roughness. Hence, surface modification of the titanium dioxide thin film was performed at a fixed a discharge power of 5 W, for 4 hours at 400° C. FIGS. 4A-4C show an ESCA spectrum of the titanium dioxide thin film deposited at 5 W. $Ti^{4+}$ peaks of $TiO_2$ were observed at 458.8 eV (2p3/2) and 464.7 eV (2p1/2), and an O1s peak corresponding to the Ti—O bonding of $TiO_2$ was observed at 530.4 eV. FIGS. 5A-5D show an ESCA spectrum of the nitrogen-doped titanium dioxide thin film. Ti and O1s peaks were observed at positions similar to those of the titanium dioxide thin film. Further, the N1s peak at 399 eV with a content of 0.8% confirms that nitrogen was doped into the surface of titanium dioxide.

Figure 6:
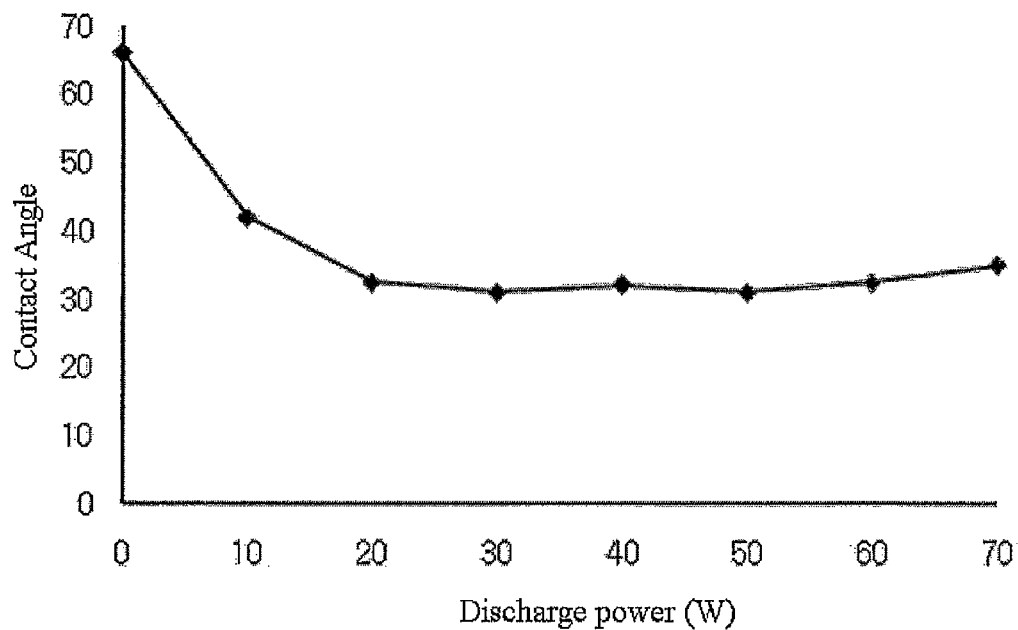
FIG. 6 shows the change of contact angle depending on the discharge power applied for modification.

(c) Analysis of Surface Modification of Titanium Dioxide Thin Films at Different Discharge Powers After the surface modification of the titanium dioxide thin film using $H_2O$ in order to introduce hydroxyl groups, contact angle was measured after washing the surface once with distilled water. The relationship between the contact angle and the discharge power applied for the modification is shown in FIG. 6. On the whole, the contact angle was smaller than 40°, which indicates that hydrophilic functional groups were introduced on the surface. The contact angle was lower at a discharge power range of 20 to 50 W, and the contact angle increased at a discharge power of 60 W or above. It may be because the titanium dioxide thin film was partly etched or the structure of titanium dioxide was changed at the high discharge power.

Figure 7:
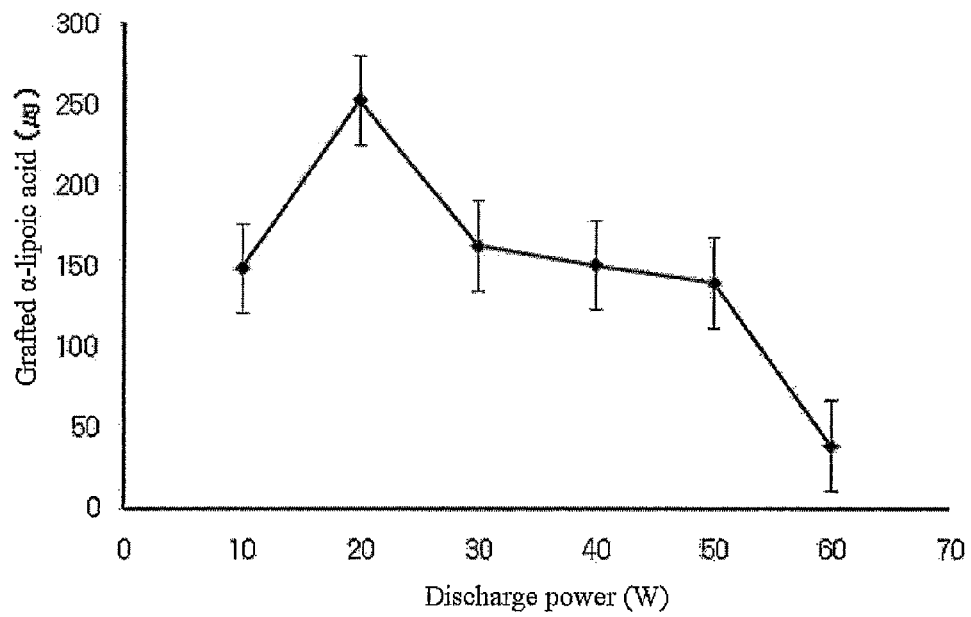
FIG. 7 shows the quantity of attached α-lipoic acid depending on the discharge power applied for modification.

After binding a drug on the surface of the stent that had been modified with hydroxyl groups, the amount of the bound drug was calculated using the calibration curves. FIG. 7 shows the quantity of attached α-lipoic acid depending on the discharge power. As seen from FIG. 7, the attached amount was largest at 250 μg when the discharge power applied for the surface modification was 20 W. The thin films modified at 10, 30, 40 and 50 W showed attached amounts of about 150 μg. In contrast, the attached amount decreased remarkably at 60 W, which suggest that the surface of titanium dioxide might have been deformed or etched by the plasma. Therefore, it can be seen that a 10 to 50 W is ideal for modification of the titanium dioxide thin film using water.

Figure 8:
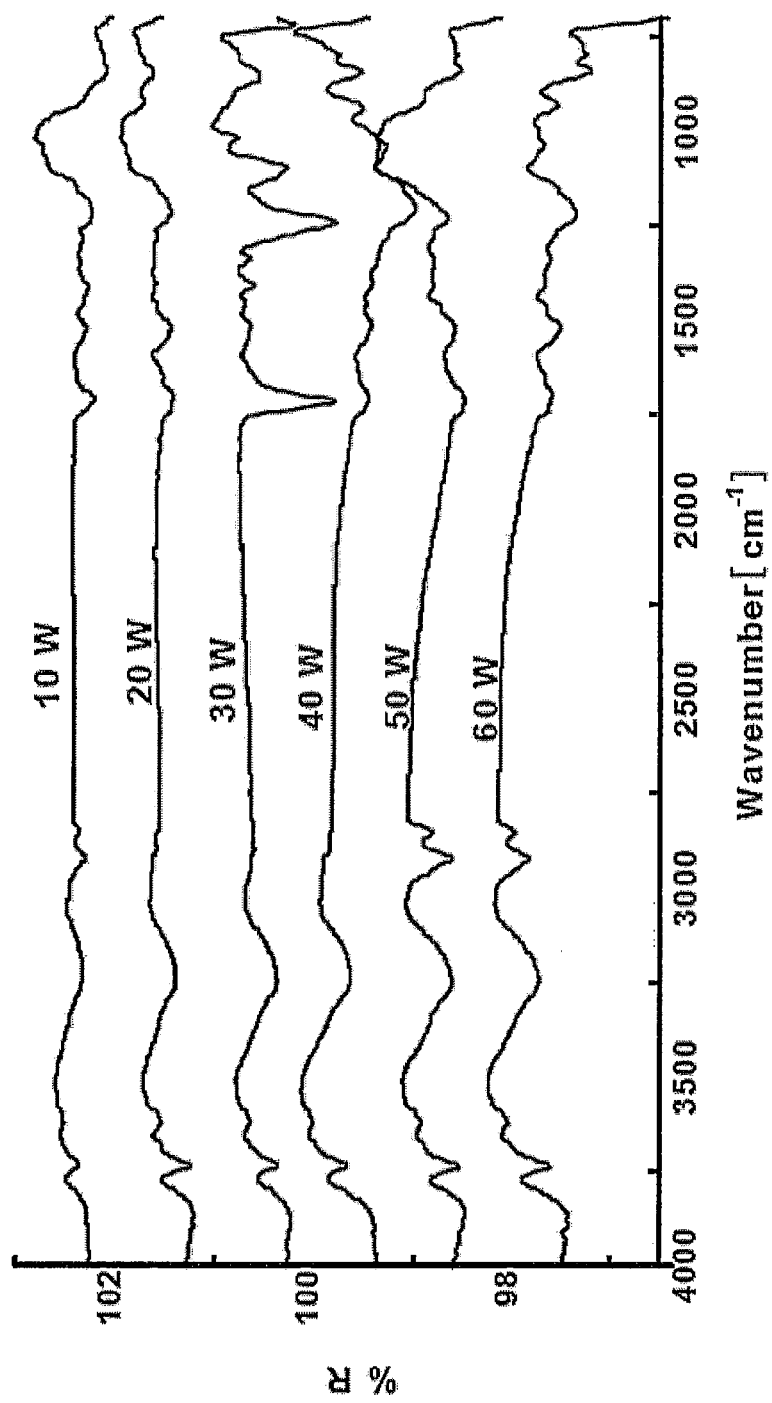
FIG. 8 shows attenuated total reflectance (ATR) Fourier transform infrared spectroscopy (FT-IR) spectra after attachment of α-lipoic acid depending on the discharge power applied for modification.
Figure 9A:
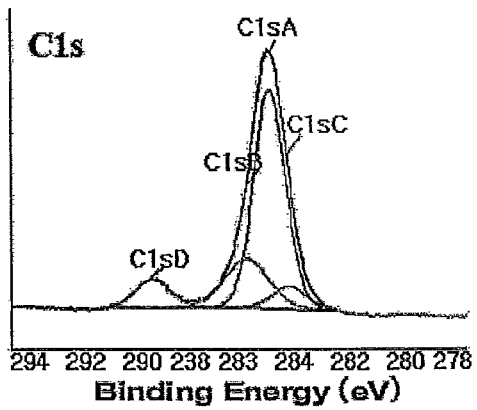
FIG. 9A shows an ESCA spectrum of an α-lipoic acid attached titanium dioxide surface.
Figure 9B:
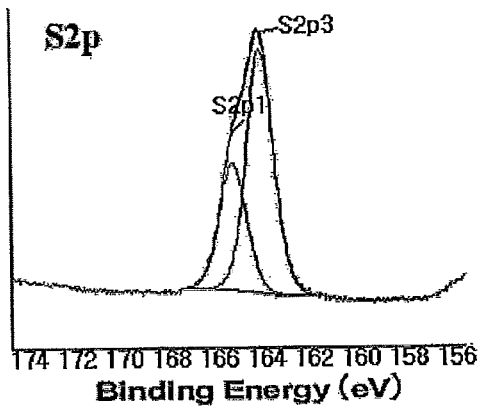
FIG. 9B shows a magnified view of an ESCA spectrum of an α-lipoic acid attached titanium dioxide surface.
Figure 9C:
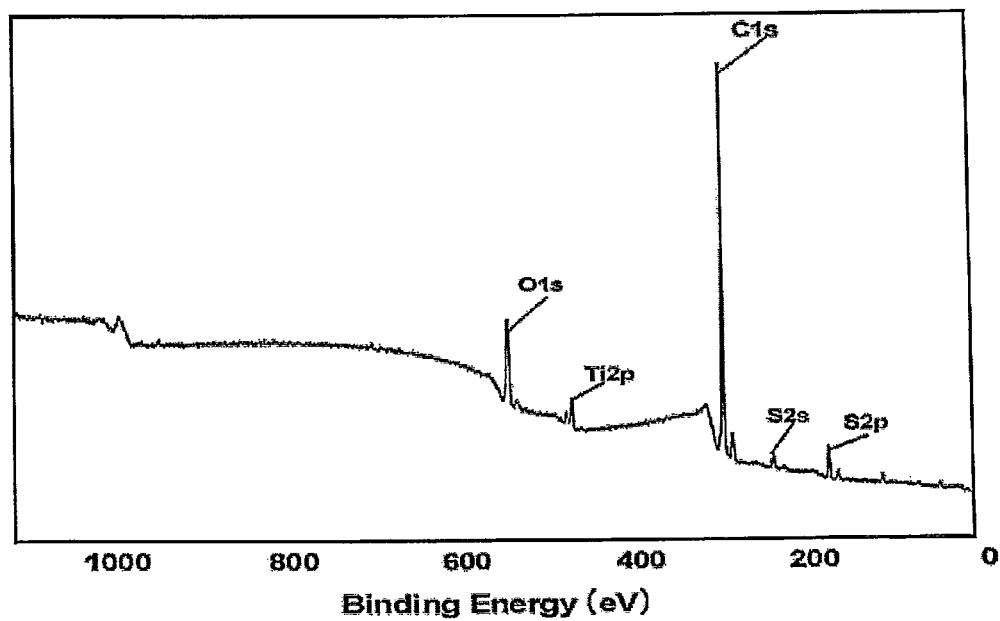
FIG. 9C shows an ESCA spectrum of an α-lipoic acid attached titanium dioxide surface.
Figure 10A:
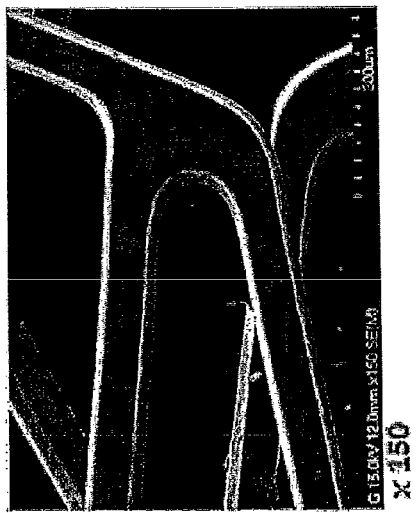
FIGS. 10A-10D show scanning electron micrographs (SEMs) of an α-lipoic acid attached stent, according to embodiments of the invention.
Figure 10B:
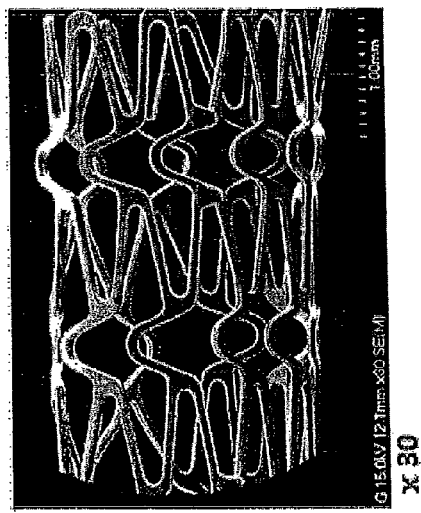
Figure 10C:
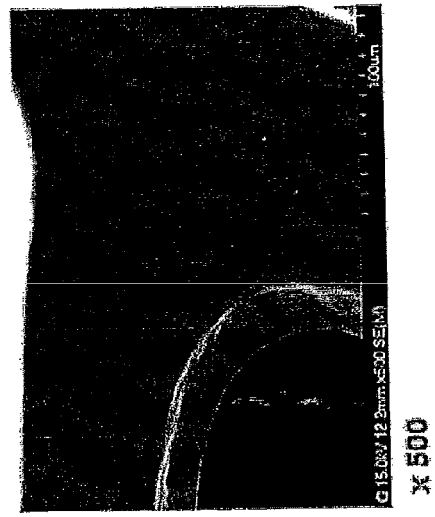
Figure 10D:
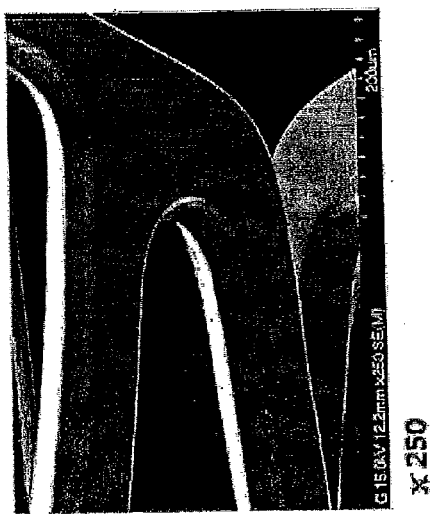
Figure 11A:
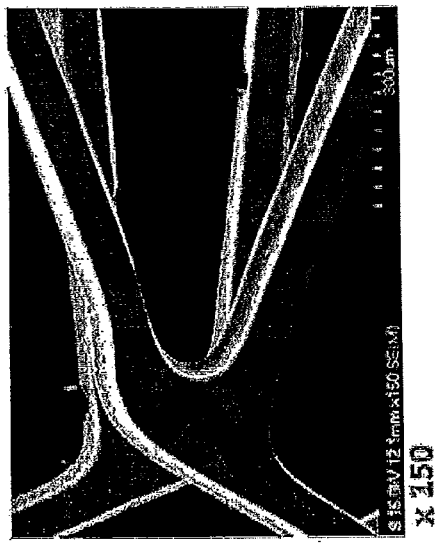
FIGS. 11A-11D show SEMs of an α-lipoic acid attached stent after ultrasonic cleaning for 30 minutes, according to embodiments of the invention.
Figure 11B:
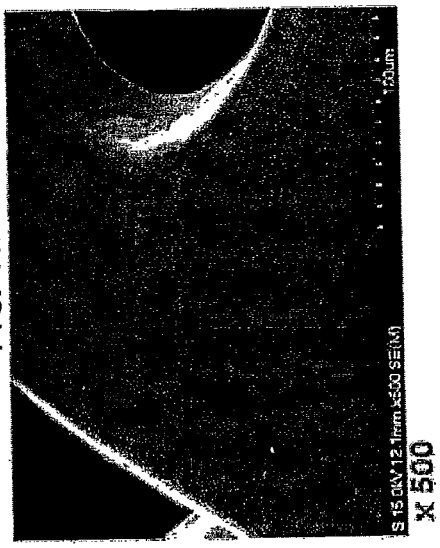
Figure 11C:
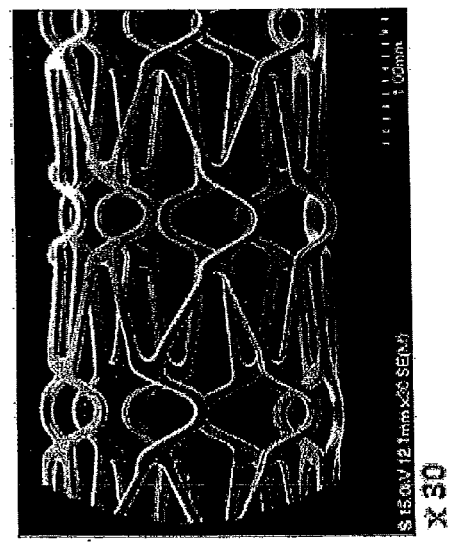
Figure 11D:
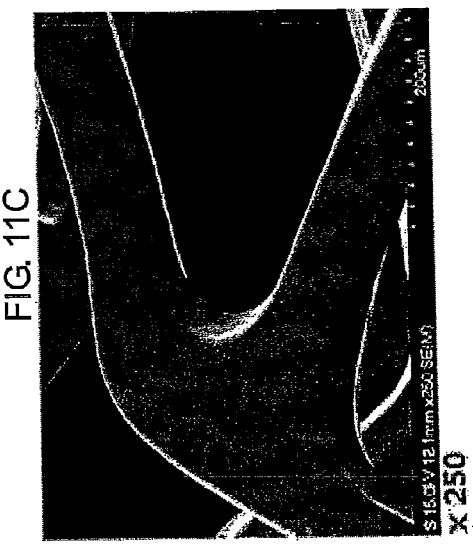

(d) Analysis of Chemical Structure and Physical Properties of Drug Attached Surface Upon the modification of the coated titanium dioxide thin film at a discharge power of 10 to 60 W followed by the addition of the drug, the chemical composition analysis by ATR FT-IR revealed that the drug was stably attached. As seen from FIG. 8, the carbonyl (C=O) peak of the ester (—C(O)O—) group, which is formed as the carboxyl group of α-lipoic acid binds with the hydroxyl (—OH) group of the titanium dioxide surface, is found at 1710 $cm^{-1}$, at all discharge powers. FIGS. 9A-9C show an ESCA spectrum of an α-lipoic acid attached titanium dioxide surface which had been deposited at 5 W and modified at 30 W using water. The surface chemical composition features S peaks, which result from the attachment of α-lipoic acid. Also, the high resolution ESCA of carbon of the spectrum shows the carbonyl peak of the ester group at 289 eV.

Figure 12:
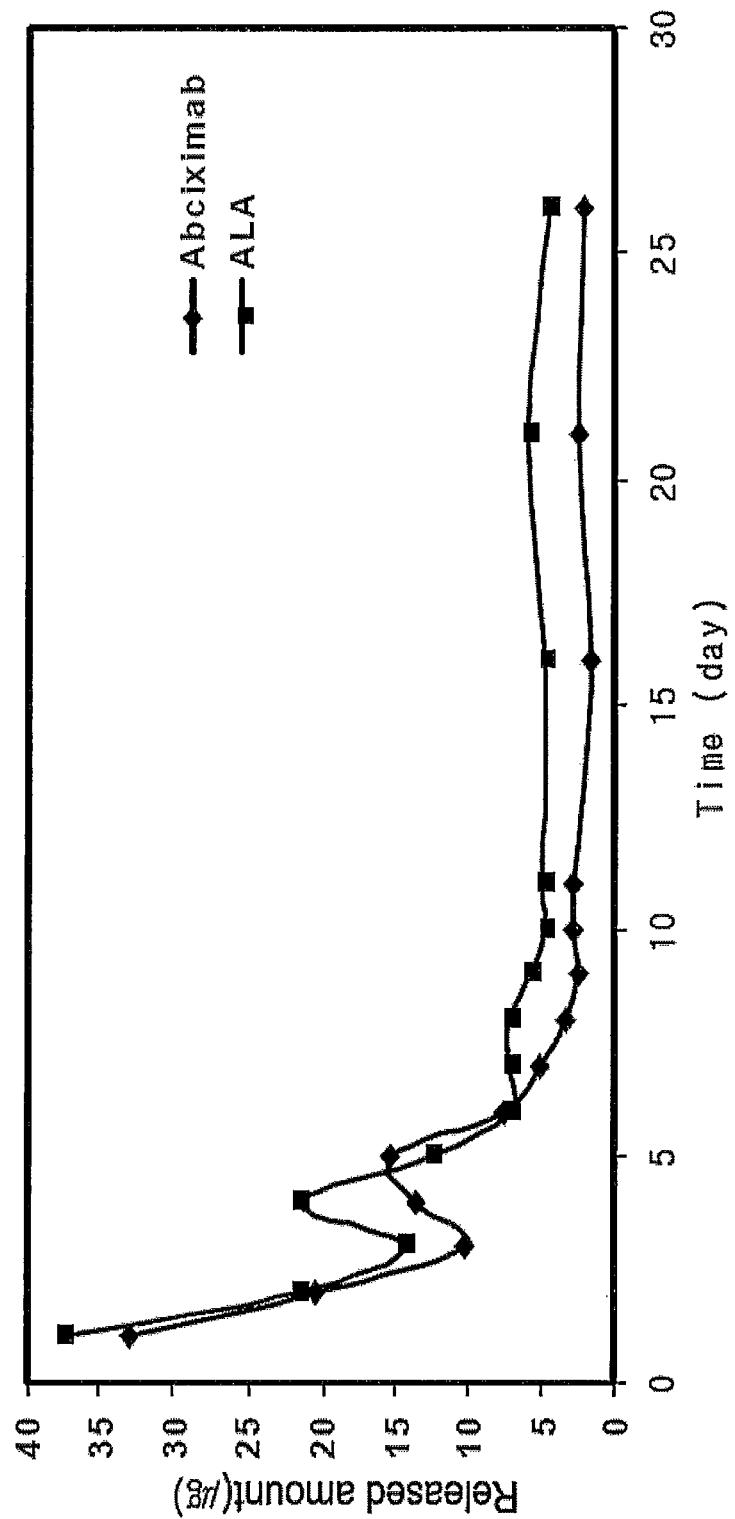
FIG. 12 shows a drug release profile of a ReoPro-α-lipoic acid attached stent.

The surface state of the α-lipoic acid attached titanium dioxide was observed by SEM. The physical state of the stent surface is very important because a torn or rough surface may result in easier blood clot formation and quick restenosis. FIGS. 10A-10D show scanning electron micrographs (SEMs) of an α-lipoic acid attached stent which had been deposited at 5 W and modified at 30 W using discharge water. It can be seen that the surface is very smooth with no tearing. The adhesion between the coated titanium dioxide thin film and the stent is important since a weak adhesion may result in easy detachment from the metal surface. In order to evaluate the adhesion between the coated surface and the stent, the α-lipoic acid attached stent to soak in 1× PBS buffer was treated using an ultrasonic cleaner for 30 minutes, after treating using an ultrasonic cleaner, the surface was observed by SEM. The result is shown in FIGS. 11A-11D. It can be seen that the stent remains stably as prior to the ultrasonic cleaning, without peeling or tearing. Therefore, it is considered that the coated thin film has a very uniform and smooth surface and adheres well to the stent surface. FIG. 12 shows a drug release profile of a ReoPro-α-lipoic acid attached stent. As seen from the figure, ReoPro and α-lipoic were consistently released for 30 days from the stent surface where the drugs were attached.

While the present invention has been described with respect to the specific embodiments, it will be apparent to those skilled in the art that various changes and modifications may be made without departing from the spirit and scope of the invention as defined in the following claims.

What is claimed is:

1. A method for manufacturing a drug-releasing stent, comprising:
   providing a titanium precursor, a carrier gas and a reactant gas in a plasma vacuum chamber and generating a plasma for 1 to 6 hours to form a titanium oxide thin film on the surface of a stent;
   providing steam or oxygen and hydrogen in the plasma vacuum chamber and generating a low-temperature plasma for 10 minutes to 2 hours to modify the surface of the titanium oxide thin film; and
   reacting the titanium oxide thin film of the stent with a drug in an acidic solution and under an inert gas atmosphere at room temperature to 100° C. for 30 minutes to 4 hours to attach the drug.

2. The method for manufacturing a drug-releasing stent according to claim 1, wherein the titanium precursor is one or more selected from a group consisting of titanium butoxide, tetraethylmethylamino titanium, titanium ethoxide, titanium isopropoxide and tetramethylheptadiene titanium.

3. The method for manufacturing a drug-releasing stent according to claim 1, wherein the carrier gas is one or more selected from a group consisting of argon and helium.

4. The method for manufacturing a drug-releasing stent according to claim 1, wherein the reactant gas is one or more selected from a group consisting of steam, ozone and oxygen.

5. The method for manufacturing a drug-releasing stent according to claim 4, wherein nitrogen gas is added to the reactant gas to form nitrogen-doped titanium oxide ($TiO_{2-x}N_x$; x is from 0.001 to 1).

6. The method for manufacturing a drug-releasing stent according to claim 1, wherein the drug is one or more selected from a group consisting of heparin, ReoPro (abciximab), α-lipoic acid, sirolimus (rapamycin), actinomycin, molsidomine, linsidomine and paclitaxel.

* * * * *